(12) United States Patent
Taarning et al.

(10) Patent No.: US 9,328,048 B2
(45) Date of Patent: May 3, 2016

(54) PROCESS FOR PREPARING KETENE IN THE PRESENCE OF A FLUIDIZED BED MATERIAL WITH A SURFACE AREA OF UP TO 600 M²/G

(71) Applicant: Haldor Topsøe A/S, Kgs. Lyngby (DK)

(72) Inventors: Esben Taarning, Frederiksberg (DK); Martin Spangsberg Holm, Oxford (GB); Christian Mårup Osmundsen, Gentofte (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/769,488

(22) PCT Filed: Feb. 25, 2014

(86) PCT No.: PCT/EP2014/053644
§ 371 (c)(1),
(2) Date: Aug. 21, 2015

(87) PCT Pub. No.: WO2014/131764
PCT Pub. Date: Sep. 4, 2014

(65) Prior Publication Data
US 2016/0009622 A1   Jan. 14, 2016

(30) Foreign Application Priority Data

Feb. 27, 2013   (WO) ............... PCT/EP2013/053977
Feb. 28, 2013   (WO) ............... PCT/EP2013/054062
Mar. 25, 2013   (WO) ............... PCT/EP2013/056284

(51) Int. Cl.
*C07C 45/89*   (2006.01)
*C07C 45/87*   (2006.01)

(52) U.S. Cl.
CPC ...................................... *C07C 45/87* (2013.01)

(58) Field of Classification Search
CPC ........................................................ C07C 45/87
USPC ........................................................ 568/302
See application file for complete search history.

(56) References Cited

U.S. PATENT DOCUMENTS 7,094,932 B2   8/2006   Majerski et al.

FOREIGN PATENT DOCUMENTS

GB            691352 A       5/1953

OTHER PUBLICATIONS

J.C. Kang et al., "Ketene Formation from the Pyrolysis of Carbohydrates", Symposium on Thermal Uses and Properties of Carbohydrates and Lignins: Papers from the Symposium held at the 172nd National Meeting of the American Chemical Society, Acad. Press, San Francisco, CA, USA, Jan. 1, 1976, pp. 261-273.

*Primary Examiner* — Sikarl Witherspoon
(74) *Attorney, Agent, or Firm* — Blank Rome LLP

(57) ABSTRACT

A Process for preparing ketene in the presence of a fluidized bed material with a surface area of up to about 600 m²/g. The process is further defined as a process for preparing ketene from a sugar or glycolaldehyde feedstock.

12 Claims, 3 Drawing Sheets

Figure 1:
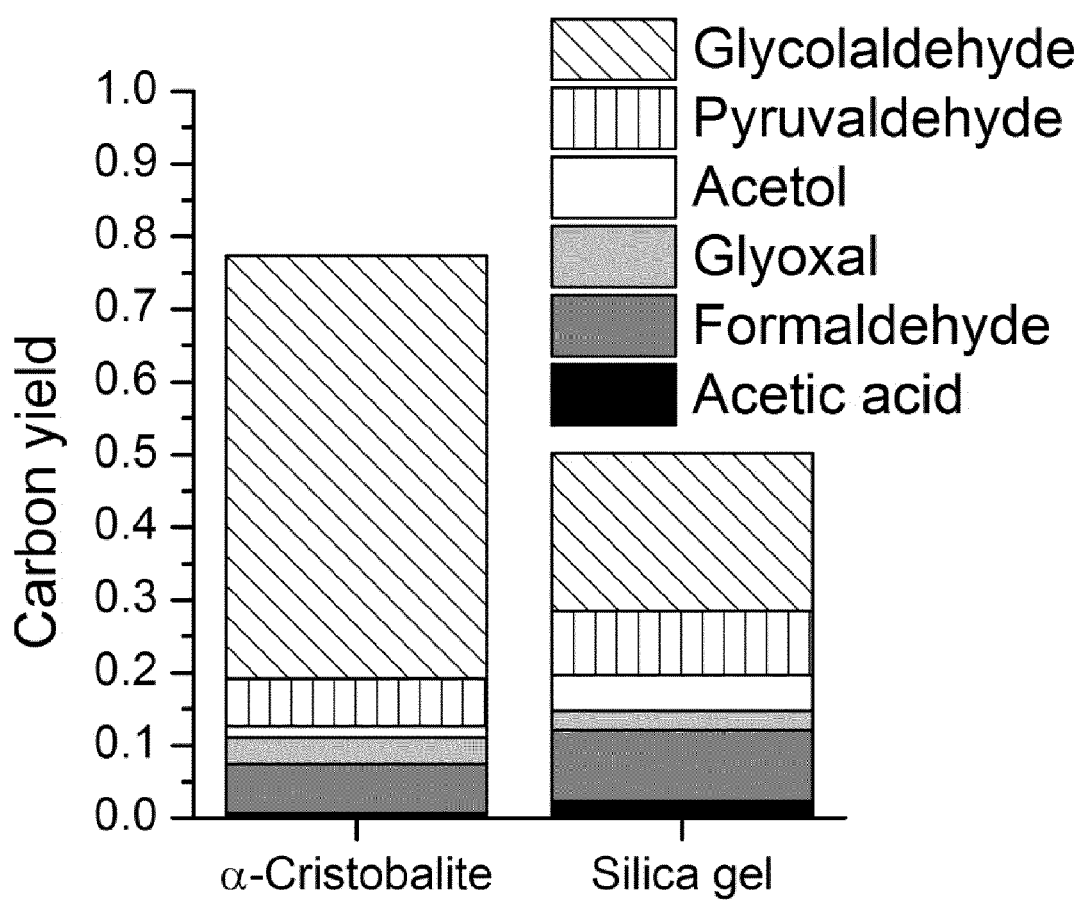

PROCESS FOR PREPARING KETENE IN THE PRESENCE OF A FLUIDIZED BED MATERIAL WITH A SURFACE AREA OF UP TO 600 M²/G

Ketene (ethenone) is a highly volatile, reactive compound that has a tendency to react with other species, such as water, therefore making it difficult to detect and quantify.

Symposium on thermal uses and properties of carbohydrates and lignins (1976) 261-273, discloses the formation of ketene from the pyrolysis of glucose via trapping experiments with deuterated water (deuterium oxide) and alkyl amines. A yield of 16% of ketene from the pyrolysis of glucose at 700° C. is disclosed; at lower reaction temperatures, such as 500 and 600° C., the yield is 2.4 and 4.2% respectively.

U.S. Pat. No. 7,094,932 discloses the pyrolysis of an aqueous solution of glucose via a fluidized bed of sand. The condensable products are quantified; the aim of the experimental is to provide an improved process for preparing a glycolaldehyde-rich solution. Although U.S. Pat. No. 7,094,932 cites 'Symposium on thermal uses and properties of carbohydrates and lignins (1976) 261-273' as disclosing the formation of ketene from glucose, no ketene product is observed in the products of the reactions disclosed in U.S. Pat. No. 7,094,932, supporting the fact that pyrolysis reaction temperatures below 700° C. are not optimal for ketene (ethenone) formation.

Ind. Eng. Chem. Res. (1994) 2904-2912, discloses the use of chromatographic grade silica, i.e. high surface area silica, to increase the selectivity of ketene formation from acetates pre-adsorbed onto silica. At lower temperatures, 573-673 K (300-400° C.), the selectivity for ketene formation from acetic acid (0.48-0.41) is higher than at higher temperatures, 773-973K (500-700° C.), (0.34-0.16). Reaction temperatures of 750 K were essential for steady state catalysis. When longer chain carboxylic acids are subjected to the reaction conditions, the longer chain ketene is formed; i.e. valeric acid forms propylketene. Smaller carbon chain compounds, e.g. propionic acid, provide the corresponding ketonisation product as the greatest yielding product.

It is therefore desirable to provide a high yielding, improved one-step catalytic process for the preparation of ketene (ethenone) from a feedstock comprising one or more sugars or glycolaldehyde. In particular, it is desirable to provide an improved process wherein ketene is obtainable in its free form and is suitable for subsequent transformations. In particular, the improved process provides a yield of ketene (ethenone) suitable for commercial viability of the process.

The process of the present invention is further defined as a process for preparing ketene from a feedstock, wherein the feedstock is pyrolysed in the presence of a fluidized bed material with a surface area of up to about 600 m²/g.

In an embodiment of the invention the feedstock may be one or more sugars or glycolaldehyde. In a preferred embodiment of the present invention the feedstock is a monosaccharide. In a more preferred embodiment of the present invention the feedstock is one or more sugars selected from the group consisting of glucose, fructose, galactose, xylose, sucrose and mannose. Preferably the feedstock is glucose.

In a preferred embodiment of the present invention the fluidized bed material has an average particle size suitable for achieving a fluidized bed.

In a preferred embodiment of the present invention the fluidized bed material has a surface area of up to about 600 m²/g. In a further preferred embodiment of the present invention the fluidized bed material has a surface area of between 200 and 600 m²/g, preferably between about 300 and 550 m²/g, more preferably between about 400 and 600 m²/g.

In a preferred embodiment of the present invention the fluidized bed material has a pore volume of up to about 0.80 ml/g, preferably between about 0.40 and 0.75 ml/g, preferably between about 0.50 and 0.70 ml/g, preferably about 0.60 and 0.70 ml/g.

In a preferred embodiment of the present invention the fluidized bed material has a silanol concentration of up to about 4.0 M, preferably between about 2.0 M and 4.0 M, preferably between about 3.0 and 4.5 M, preferably about 3.5 M and 4.0 M.

In a preferred embodiment of the present invention the fluidized bed material is silicon oxide. In a more preferred embodiment the fluidized bed material is selected from the group consisting of high surface area silica.

In a preferred embodiment of the present invention the fluidized bed material is selected from the group consisting of SiC, silica gel and silica gel calcined at 500° C.

In a preferred embodiment of the present invention the fluidized bed material is colloidal silica mixed with an oxide selected from the group consisting of $Nb_2O_5$, $TiO_2$, $ZrO_2$, $CeO_2$ and BaO.

In a preferred embodiment of the present invention the temperature of the reaction is less than about 700° C., preferably less than about 600° C., more preferably between about 500 and 600° C.

In a preferred embodiment of the present invention the reaction chamber contains a fluidized catalyst. More preferably the reaction chamber contains a fluidized catalyst and the residence time of the feedstock in the reaction chamber of the fluidized bed is between about 50 to about 150 ms.

In a preferred embodiment of the present invention the percentage yield of ketene is greater than 16%.

In a preferred embodiment of the present invention the process is run as a continuous process.

In a preferred embodiment of the present invention the feedstock is introduced into the fluidized bed reaction chamber as an aqueous solution. In a further preferred embodiment the feedstock is introduced into the fluidized bed reaction chamber as an aqueous solution comprising up to 60% by weight of the feedstock, as disclosed in U.S. Pat. No. 7,094,932. In a further preferred embodiment the feedstock is introduced into the fluidized bed reaction chamber as an aqueous solution comprising between about 10% to about 60% by weight of the feedstock. In a further preferred embodiment the feedstock is introduced into the fluidized bed reaction chamber as an aqueous solution comprising between about 10% to 30% by weight of the feedstock. In a further preferred embodiment the feedstock is introduced into the fluidized bed reaction chamber as an aqueous solution comprising about 10% by weight of the feedstock.

In a preferred embodiment of the present invention the feedstock is introduced into the fluidized bed reaction chamber as an atomized solution with a particle size of less than 10 μm.

In a preferred embodiment of the present invention the process is carried out under an inert atmosphere, e.g. an atmosphere of nitrogen.

General Experimental:

The thermolytic conversion of carbohydrates was investigated in a fluidized bed setup. The setup consists of a stainless steel reactor (i.d.: 22 mm, length: 80 cm) fitted with a gas atomizing nozzle (Spraying Systems Co.), capable of delivering the liquid feed as a fine mist into the reactor (droplet size: <10 μm). The reaction temperature was monitored with a thermocouple extending from the top of the reactor into the bed. The top of the reactor was fitted with a disengager to prevent elutriation of the bed particles. Immediately after the outlet, the gas stream was directed through a condenser kept at 1° C. to collect the liquid product. The gas phase product may be passed into a subsequent reactor and transformed into further products as illustrated in 'Ketenes' Ullman's Encyclopedia of Industrial Chemistry (2002) 171-185.

In a typical experiment, the reactor was charged with 10 ml of the bed material, having a particle size from 90 to 150 μm. A nitrogen flow of 3.5 Nl/min was used to fluidize the bed, while the reactor temperature was raised to the desired reaction temperature of between 550-600° C. When the reactor reached the desired temperature water was pumped to the nozzle, using a tube pump, at a flow rate 0.5 ml/min and injected into the bed. The liquid flow was maintained for at least 20 min to obtain a stable temperature in the bed.

The experiment was started by changing the liquid to a 10 wt % aqueous solution of the substrate, at which point the time was set as t=0. The dead time from the feed flask to the nozzle was approx. 20 min. Collection of the liquid product was started at t=30 min. The condensed liquid was collected over the entirety of the experiment to calculate mass balances. Each experiment was run for at least 6 hr.

Liquid products were quantified by HPLC analysis (Agilent, 1200 Series). The analytes were separated on a BioRad Aminex HPX-87H column operating at 65° C. The eluent was a 0.005 M aqueous $H_2SO_4$, at a flow rate of 0.6 ml/min. The analytes were quantified using a RI detector against standard samples. Products were identified either by matching retention time with a known standard, or if possible by GC-MS analysis on an Agilent Technologies 6890 Plus series gas chromatograph with an Agilent Technologies 5973A series mass selective detector.

Analysis of the gas phase products was performed by directing part of the gas stream, after the condenser, into a mass spectrometer (IPI, GAM 200 Multi Component Gas Analyser).

Measurement of Fluidized Bed Material Silanol Concentration:

The dehydroxylation behavior of silica was measured on a Mettler TGA/DSC 1; the sample was dehydrated at 150° C. for 60 min in a flow of 20% $O_2$, 26% He and 54% Ar at 50 ml/min; this gas flow was maintained for the duration of the analysis. The temperature was lowered to 40° C. and then increased to 1500° C. at 5° C./min, while monitoring the weight of the sample.

|  | BET surface are ($m^2$/g) | Pore volume (ml/g) | Silanol concentration (M) |
|---|---|---|---|
| Silica gel (SG60) | 517 | 0.68 | 3.60 |
| Silica gel (calcined at 1000° C.) | 4 | 0.01 | 0.20 |
| alpha-cristobalite | 4 | 0.01 | 0.00 |

The first two parameters (BET surface area and Pore Volume) are determined by N2 sorption. The silanol concentration is measured by a combination of TGA and Hg porosimetry.

EXAMPLE 1

The experimental procedure was followed according to the general experimental, where the fluid bed material was a silica compound [α-cristobalite; Sigma Alrich named as Silicon dioxide (quartz, cristabolite), product number: 84878], the substrate was glucose (D-glucose monohydrate; Sigma Aldrich). The reactor temperature was 550° C.

EXAMPLE 2

The experimental procedure was followed according to the general experimental, where the fluidized bed material was a silica compound [silica gel; SG60 from Merck], the substrate was glucose (D-glucose monohydrate; Sigma Aldrich). The reactor temperature was 560° C.

EXAMPLE 3

The experimental procedure was followed according to the general experimental, where the fluidized bed material was a silica compound [silica gel; SG60 from Merck) calcined at 500° C.], the substrate was glucose (D-glucose monohydrate; Sigma Aldrich).

EXAMPLE 4

The experimental procedure was followed according to the general experimental, where the fluidized bed material was a silica compound [silica gel; SG60 from Merck], the substrate was glucose (D-glucose monohydrate; Sigma Aldrich). However, the reactor temperature was 515° C.

EXAMPLE 5

The experimental procedure was followed according to the general experimental, where the fluidized bed material was a silica compound [silica gel; SG60 from Merck], the substrate was glucose (D-glucose monohydrate; Sigma Aldrich). However, the reactor temperature was 590° C.

EXAMPLE 6

The experimental procedure was followed according to the general experimental, where the fluidized bed material was a silica compound [silica gel; SG60 from Merck], the substrate was glucose (D-glucose monohydrate; Sigma Aldrich). However, the liquid feed was a 30 wt % aqueous solution of the substrate, i.e. the concentration of the substrate in water was 30 wt % of glucose.

EXAMPLE 7

The experimental procedure was followed according to the general experimental, where the fluidized bed material was prepared from a mixture of colloidal silica with a colloidal metal oxide selected from the group consisting of $Nb_2O_5$, $TiO_2$, $ZrO_2$, $CeO_2$ and BaO (all colloidal metal oxides were obtained from Alfa Aesar). The colloidal silica and colloidal metal oxide mix [$TiO_2$, $ZrO_2$ or $CeO_2$] was prepared by mixing colloids of the desired oxides with colloidal silica (Ludox AS-30 from Sigma-Aldrich) in a ratio of 1:9 oxide to silica, and evaporating to dryness, followed by calcination at 1000° C. An aqueous solution of $BaNO_3$ was used to prepare the BaO/colloidal silica mix. $Nb_2O_5$ was prepared by impregnation of $NbCl_5$ onto silica gel [SG60, Merck] by incipient wetness impregnation and calcined at 1000° C.

TABLE 1

Carbon yield and composition of the liquid condensate.

| Liquid Condensate Composition | Example | | | | |
|---|---|---|---|---|---|
| | 1 | 2 | 4 | 5 | 6 |
| Glyoxal | 0.037 | 0.026 | 0.029 | 0.028 | 0.028 |
| Pyruvaldehyde | 0.065 | 0.088 | 0.110 | 0.080 | 0.090 |
| Glycolaldeyde | 0.582 | 0.217 | 0.292 | 0.213 | 0.385 |
| Formaldehyde | 0.067 | 0.098 | 0.090 | 0.092 | 0.072 |
| Acetic Acid | 0.007 | 0.024 | 0.018 | 0.021 | 0.011 |
| Acetol | 0.016 | 0.050 | 0.044 | 0.033 | 0.027 |

TABLE 2

Comparison of the MS signal of the gas phase components for Examples 1, 2, 4, 5 and 6 where the intensity of the MS signal of Examples 2, 4, 5 and 6 are normalized to the signal obtained in Example 1.

| Gas Phase MS signal | Example | | | | |
|---|---|---|---|---|---|
| | 1 | 2 | 4 | 5 | 6 |
| Acetone (m/z = 58) | 1 | 6.25 | 2.9 | 5.3 | 7.6 |
| Ketene (m/z = 42) | 1 | 3.17 | 1.6 | 3.4 | 4.8 |

Table 2 illustrates that an increase in surface area of the fluidized bed material increase the amount of acetone and ketene produced.

FIGURES

FIG. 1: Carbon yield and product composition of liquid condensate of pyrolysis of 10 wt % aqueous solution of glucose according to Examples 1 and 2 wherein α-cristobalite or silica gel are used as fluidized bed material.

Figure 2:
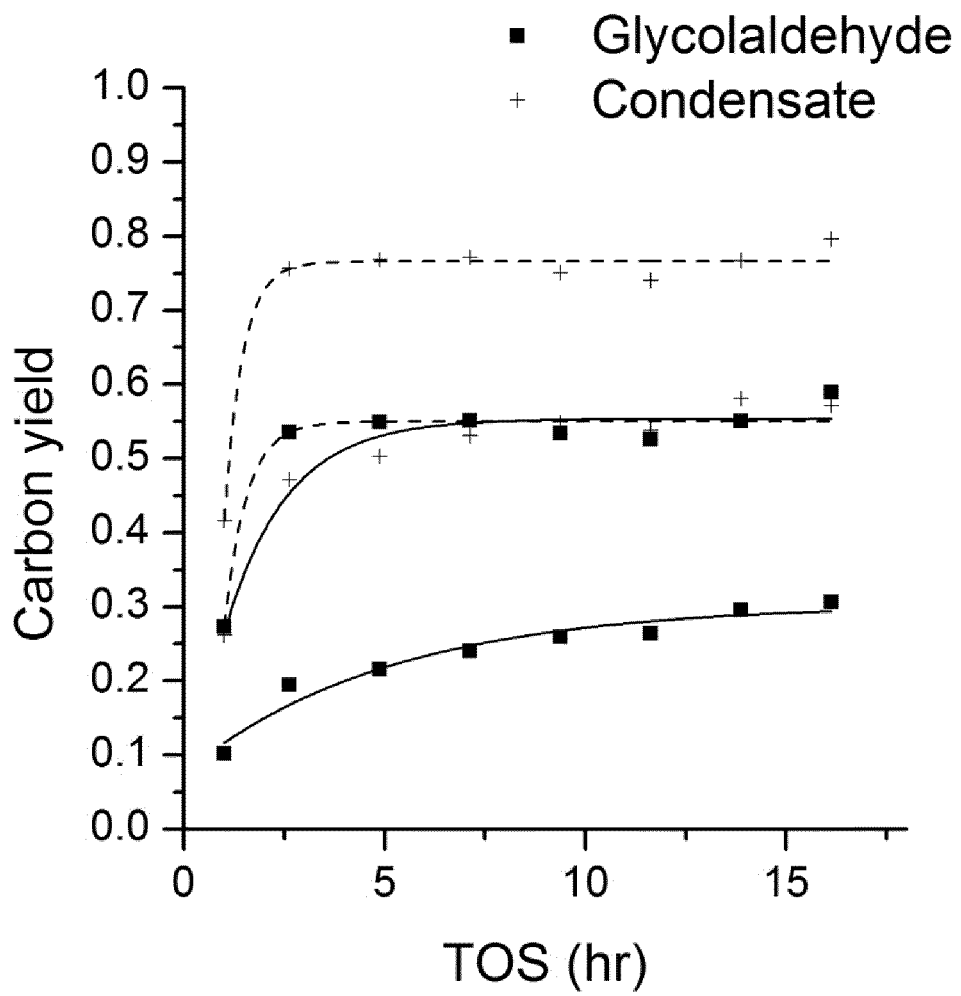

FIG. 2: Carbon yield of condensed liquid products of Examples 2 [Silica gel as received] and 1 [silica gel calcined at 1000° C. is equivalent to α-cristobalite], as a function of time of the reaction.

Figure 3:
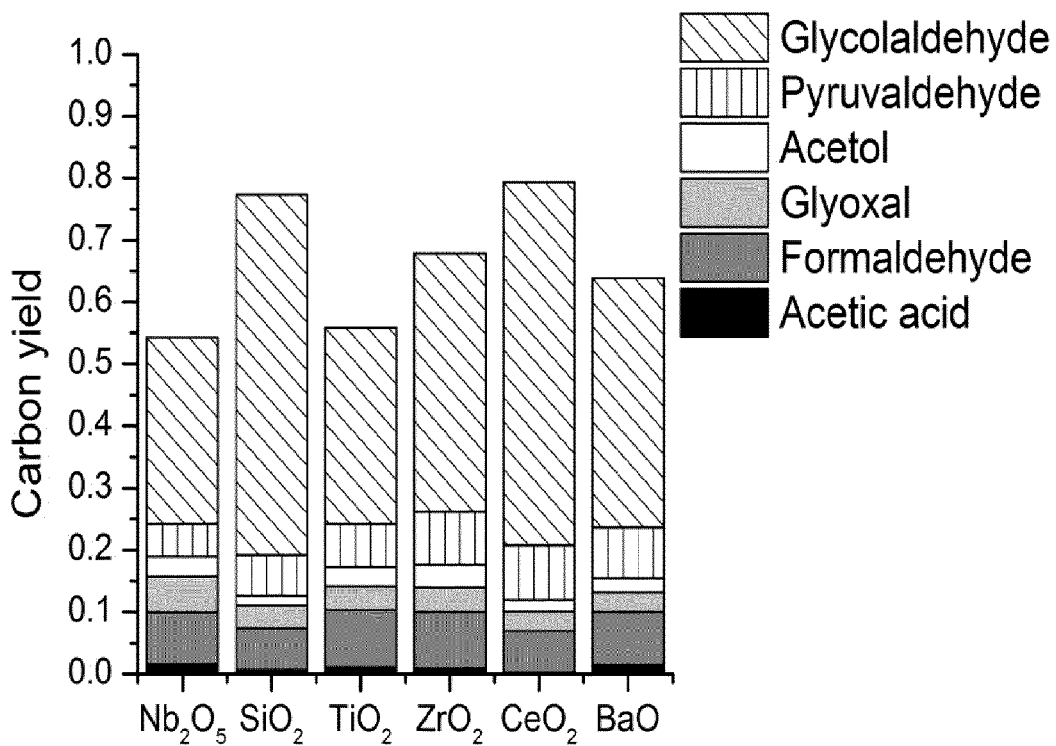

FIG. 3: Carbon yield and product composition of pyrolysis of 10 wt % aqueous solution of glucose according to Example wherein colloids of acidic and basic oxides are mixed with colloidal silica and used as bed material.

FIGS. 1 to 3 illustrate the increased yield of acetic acid produced as the surface area of the fluidized bed material increases. An increase in acetic acid yield correlates to an increase in ketene yield as ketene is hydrated to acetic acid.

The invention claimed is:

1. A process for preparing ketene from a feedstock wherein the feedstock is pyrolysed in the presence of a fluidized bed material, wherein the surface area of the fluidized bed material is up to 600 $m^2$ per gram and the feedstock is selected from one or more of the group consisting of glucose, fructose, galactose, xylose, sucrose and mannose and glycolaldehyde.

2. A process according to claim 1, wherein the fluidized bed material is selected from the group consisting of SiC, silica gel, and silica gel calcined at 500° C.

3. A process according to claim 1, wherein the fluidized bed material is colloidal silica mixed with an oxide selected from the group consisting of $Nb_2O_5$, $SiO_2$, $TiO_2$, $ZrO_2$, $CeO_2$ and BaO.

4. A process according to claim 1, wherein the temperature of the reaction is less than 700° C.

5. A process according to claim 1, wherein the reaction chamber is a fluidized bed.

6. A process according to claim 1, wherein the residence time of the material in the reaction chamber of the fluidized bed is up to 150 ms.

7. A process according to claim 1, wherein the percentage yield of ketene is greater than 16%.

8. A process according to claim 1, wherein the feedstock is introduced into the fluidized bed reaction chamber as an aqueous solution.

9. A process according to claim 1, wherein the feedstock is introduced into the fluidized bed reaction chamber as an aqueous solution comprising up to 60% by weight of feedstock.

10. A process according to claim 1, wherein the feedstock is introduced into the fluidized bed reaction chamber as an atomized solution with a particle size of less than 10 μm.

11. A process according to claim 1, wherein the process is carried out under an inert atmosphere of nitrogen.

12. A process according to claim 1, wherein the ketene is ethenone.

* * * * *